(12) United States Patent
Bartolozzi et al.

(10) Patent No.: US 9,656,960 B2
(45) Date of Patent: May 23, 2017

(54) INHIBITORS OF MICROSOMAL TRIGLYCERIDE TRANSFER PROTEIN AND APO-B SECRETION

(71) Applicants: Alessandra Bartolozzi, Somerville, MA (US); Stewart Campbell, Framingham, MA (US); Hope Foudoulakis, Framingham, MA (US); Enoch Kim, Boston, MA (US); Paul Sweetnam, Marblehead, MA (US); Yingfei Yang, Belmont, MA (US)

(72) Inventors: Alessandra Bartolozzi, Somerville, MA (US); Stewart Campbell, Framingham, MA (US); Hope Foudoulakis, Framingham, MA (US); Enoch Kim, Boston, MA (US); Paul Sweetnam, Marblehead, MA (US); Yingfei Yang, Belmont, MA (US)

(73) Assignee: Surface Logix, Inc., Brighton, MA (US)

( * ) Notice: Subject to any disclaimer, the term of this patent is extended or adjusted under 35 U.S.C. 154(b) by 0 days.

(21) Appl. No.: 14/660,453

(22) Filed: Mar. 17, 2015

(65) Prior Publication Data
US 2016/0039765 A1 Feb. 11, 2016

Related U.S. Application Data

(63) Continuation of application No. 11/407,500, filed on Apr. 19, 2006, now Pat. No. 8,980,915.
(60) Provisional application No. 60/672,778, filed on Apr. 19, 2005, provisional application No. 60/755,390, filed on Dec. 30, 2005.

(51) Int. Cl.
| | | |
|---|---|---|
| A61K 31/472 | (2006.01) | |
| C07D 217/06 | (2006.01) | |
| A61K 31/18 | (2006.01) | |
| A61K 31/47 | (2006.01) | |
| C07D 417/04 | (2006.01) | |
| A61K 31/4725 | (2006.01) | |
| A61K 45/06 | (2006.01) | |

(52) U.S. Cl.
CPC ............ *C07D 217/06* (2013.01); *A61K 31/18* (2013.01); *A61K 31/47* (2013.01); *A61K 31/472* (2013.01); *A61K 31/4725* (2013.01); *A61K 45/06* (2013.01); *C07D 417/04* (2013.01)

(58) Field of Classification Search
USPC ......................................... 514/307, 309, 310
See application file for complete search history.

(56) References Cited

U.S. PATENT DOCUMENTS

| | | | |
|---|---|---|---|
| 5,198,462 A | 3/1993 | Natsugari et al. | |
| 5,919,795 A * | 7/1999 | Chang .................. | C07D 217/04 514/310 |
| 6,121,283 A | 9/2000 | Chang et al. | |
| 6,878,707 B2 | 4/2005 | Ksander | |
| 8,980,915 B2 | 3/2015 | Bartolozzi et al. | |

FOREIGN PATENT DOCUMENTS

| | | |
|---|---|---|
| EP | 1099442 A2 | 5/2001 |
| EP | 1181954 | 2/2002 |
| JP | H11-514964 | 12/1999 |
| JP | 2003-231633 | 8/2003 |
| RU | 97115677 | 7/1999 |
| RU | 98115572 | 7/2000 |
| WO | WO 96/26205 | 8/1996 |
| WO | WO 96/40640 | 12/1996 |
| WO | WO-97/26240 | 7/1997 |
| WO | WO 98/23593 | 6/1998 |
| WO | WO 01/77077 | 10/2001 |
| WO | WO 02/20501 | 3/2002 |
| WO | WO 03/045921 | 6/2003 |
| WO | WO 2005/080373 | 9/2005 |

OTHER PUBLICATIONS

Chandler, C.E. et al., "CP-346086: an MTP inhibitor that lowers plasma cholesterol and triglycerides in experimental animals and in humans", Journal of Lipid Research, vol. 44, pp. 1887-1901 (2003).
Extended European Search Report dated Mar. 12, 2010, from corresponding EPO Application No. EP06751011.5.
Opposition filed in the name of ALAFAR dated May 21, 2008, in corresponding Ecuador Patent Application No. SP-07-7913 (English translation).
Opposition filed in the name of ASIFAN dated Jun. 20, 2008, in corresponding Costa Rica Patent Application No. 9528 (with partial English translation).
Georgia Search Report mailed Jun. 24, 2008, in corresponding Georgian Patent Application No. AP 2006 010378 (English translation).
International Search Report for PCT/US2006/015146, filed on Apr. 19, 2006.
Japanese Office Action mailed Apr. 17, 2012 in corresponding Japanese Patent Application No. 2008507927 (English translation).
Kim et al., "A Small-Molecule Inhibitor of Enterocytic Microsomal Triglyceride Transfer Protein, SLx-4090: Biochemical, Pharmacodynamic, Pharmacokinetic, and Safety Profile", The Journal of Pharmacology and Experimental Therapeutics, vol. 337, No. 3, pp. 775-785, 2011.
Ksander, G.M. et al., "Diaminoindanes as Microsomal Triglyceride Transfer Protein Inhibitors", J. Med. Chem., 44, 4677-4687 (2001).
Williams, S.J. et al., "Novel microsomal triglyceride transfer protein inhibitors", Expert Opin. Ther. Patents 13(4), pp. 479-488 (2003).

* cited by examiner

*Primary Examiner* — Pancham Bakshi
(74) *Attorney, Agent, or Firm* — Bryan D. Zerhusen; Locke Lord LLP

(57) ABSTRACT

The present invention relates to compounds which are inhibitors of microsomal triglyceride transfer protein and/or apolipoprotein B (Apo B) secretion. These compounds can be useful for the prevention and treatment of various diseases, particularly atherosclerosis and its clinical sequelae, for lowering serum lipids, and related ailments. The invention further relates to pharmaceutical compositions comprising the compounds and to methods of treating diseases, such as hypertriglyceridemia, hyperchylomicronemia, atherosclerosis, obesity, and related conditions using the compounds. A method for decreasing apolipoprotein B (apo B) secretion is also provided.

8 Claims, 5 Drawing Sheets

INHIBITORS OF MICROSOMAL TRIGLYCERIDE TRANSFER PROTEIN AND APO-B SECRETION

CROSS REFERENCE TO RELATED APPLICATIONS

This application claims the benefit of U.S. provisional patent application No. 60/672,778, filed Apr. 19, 2005, and 60/755,390, filed Dec. 30, 2005. The contents of each of these applications are incorporated herein by reference in their entireties.

FIELD OF THE INVENTION

The present invention relates to compounds which are inhibitors of microsomal triglyceride transfer protein and/or apolipoprotein B (Apo B) secretion. These compounds can be useful for the prevention and treatment of various diseases, particularly atherosclerosis and its clinical sequelae, for lowering serum lipids, and related ailments. The invention further relates to pharmaceutical compositions comprising the compounds and to methods of treating diseases, such as hypertriglyceridemia, hyperchylomicronemia, atherosclerosis, obesity, and related conditions using the compounds. A method for decreasing apolipoprotein B (apo B) secretion is also provided.

BACKGROUND OF THE INVENTION

Microsomal triglyceride transfer protein (MTP) catalyzes the transport of triglyceride, cholesteryl ester, and phospholipids. MTP has been identified as an agent that may be involved in the assembly of Apo B-containing lipoproteins and biomolecules that contribute to the formation of atherosclerotic lesions. Compounds that can inhibit MTP and/or inhibit Apo B secretion can be useful in the treatment of atherosclerosis and related diseases (see, e.g., U.S. Pat. No. 5,919,795, incorporated herein by reference). These compounds are also useful in the treating diseases or conditions in which, by inhibiting MTP and/or Apo B secretion, serum cholesterol and triglyceride levels are reduced. Examples of these diseases or conditions include hypertriglyceridemia, hypercholesterolemia, pancreatits, and obesity; and hyperchylomicronemia and hyperlipidemla associated with pancreatitis, obesity, and diabetes.

Therefore, there is a need for compounds that inhibit MTP that are effective in treating diseases or conditions, such as atherosclerosis and related diseases, and/or can provide an effective lowering of serum apo B in mammals or humans.

SUMMARY OF THE INVENTION

In one aspect, the present invention provides compounds of Formula I:

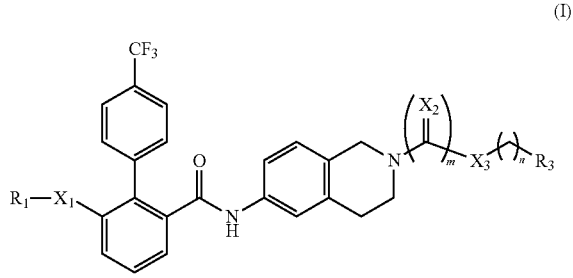

(I)

wherein
$R_1$ is alkyl (optionally substituted, e.g., with one to three substituents, e.g., halogen, amino, or alkoxy groups), $R_4R_5NC(O)CH_2$, cycloalkyl, heterocyclyl, or heterocyclylalkyl;

$X_1$ is a direct bond, O, S, —N($R_6$)—, C(O)N$R_6$, or N($R_6$)C(O);
$X_2$ is O, —N($R_6$)—, or S;
$X_3$ is a direct bond, O, —N($R_6$)—, —CH$_2$—, arylene, or S;
$R_3$ is H, alkyl, cycloalkyl, heterocyclyl, aryl, heteroaryl, heteroalkyl, aralkyl, alkylcarbonyl, alkoxycarbonyl, arylcarbonyl, aryloxycarbonyl, —OH, alkoxy, aryloxy, —SH, thioalkyl, thioaryl, or NR$_4$R$_5$;
$R_4$ and $R_5$ are, independently for each occurrence, H, alkyl, cycloalkyl, heterocyclyl, aryl, heteroaryl, heteroalkyl, aralkyl, aminocarbonyl, alkylcarbonyl, alkoxycarbonyl, arylcarbonyl, or aryloxycarbonyl;
$R_6$ is, independently for each occurrence, H or alkyl;
m is 0 or 1; and
n is an integer from 0 to 3;
provided that if m is 0, $X_3$ is a direct bond or CH$_2$;
or a pharmaceutically acceptable salt, solvate, ester or hydrate thereof.

In certain preferred embodiments, $X_1$ is O. In certain preferred embodiments, $R_1$ is alkyl, more preferably methyl, ethyl, or isopropyl. In certain preferred embodiments, $R_1$ and $X_1$ taken together form a moiety selected from the group consisting of:

H$_3$C—O—, CH$_3$CH$_2$—O—, (CH$_3$)$_2$CH—O—,

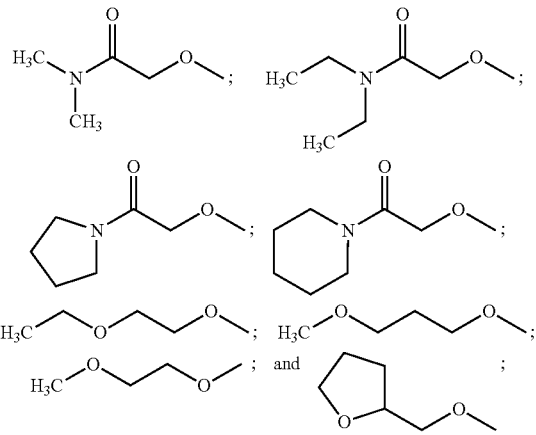

most preferably, $R_1$ and $X_1$ taken together form CH$_3$—O—.

In certain preferred embodiments, m is 1. In certain preferred embodiments, when m is 1, $X_3$ is O or NH. In certain preferred embodiments, n is 0, 1 or 2. In certain preferred embodiments, $R_3$ is aryl, more preferably unsubstituted or substituted phenyl. In other preferred embodiments, $R_3$ is cycloalkyl, heterocyclyl, heteroaryl, or alkoxy. In certain preferred embodiments, the moiety

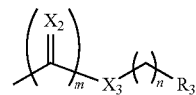

represents one of the following groups:

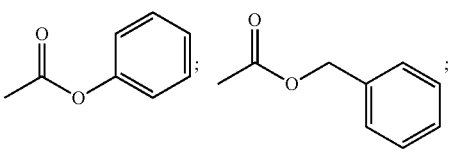

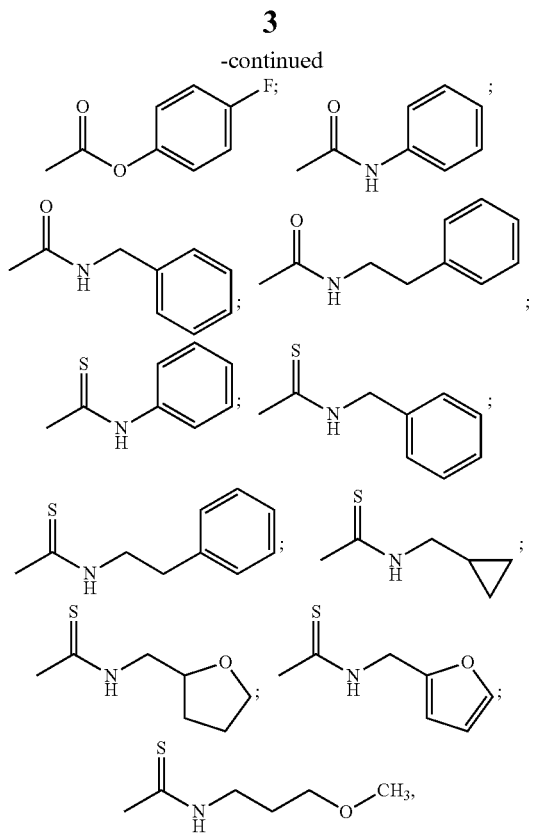

In another embodiment, the invention provides compounds represented by Formula II:

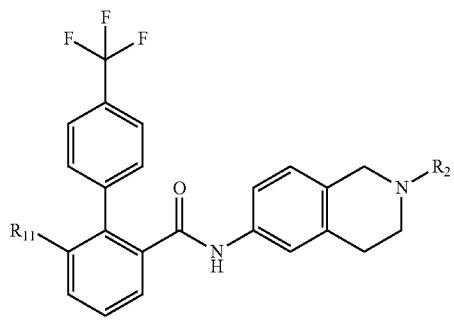

wherein $R_{11}$ is selected from:
H; $H_3C$—O—,

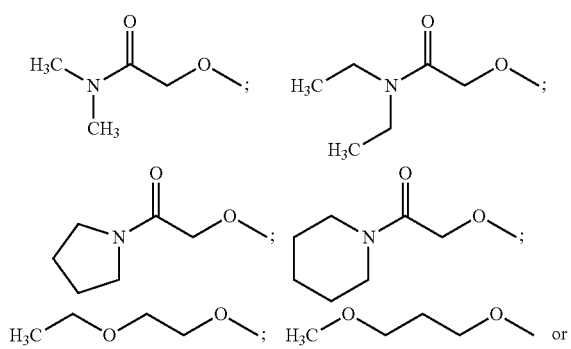

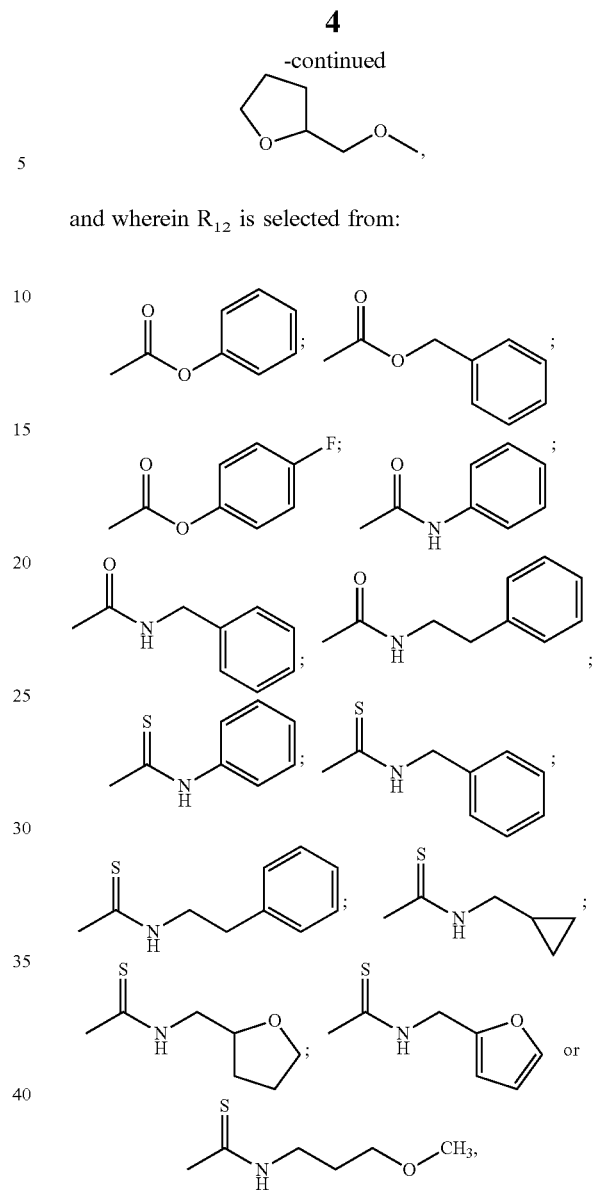

and wherein $R_{12}$ is selected from:

and pharmaceutically acceptable salts, esters, isomers, or solvate thereof.

In certain preferred embodiments, $R_{11}$ is —$OCH_3$. In certain preferred embodiments, $R_{11}$ is not H.

Among the more preferred compounds of Formula I and/or II of the present invention are the following compounds:

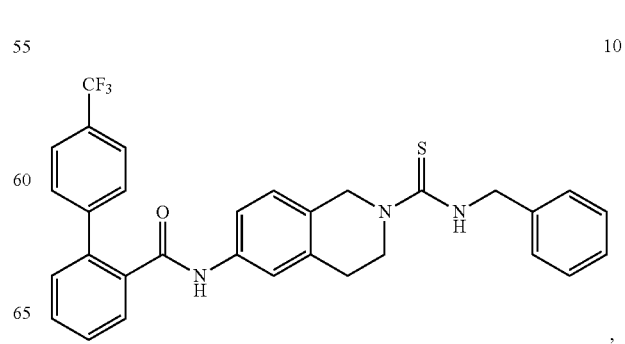

11

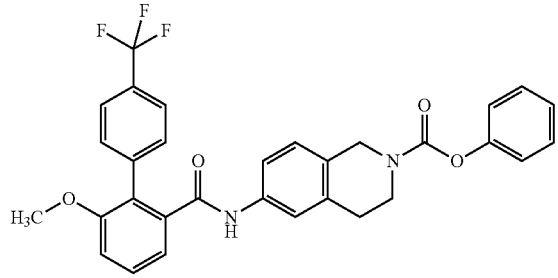

13

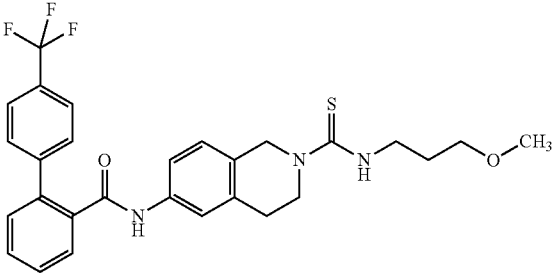

15

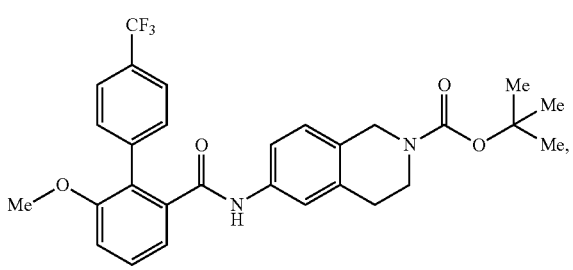

16

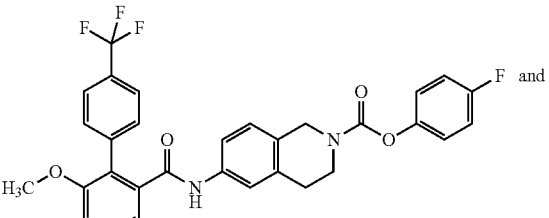

6

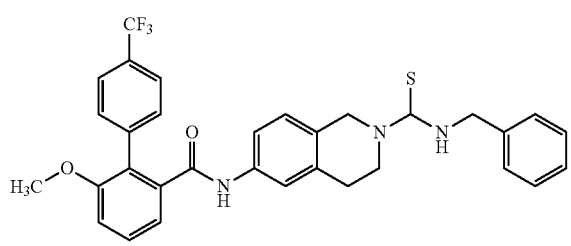

17

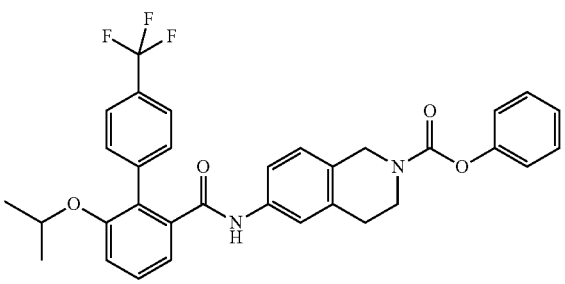

12

14 and pharmaceutically acceptable salts, esters, isomer and hydrates thereof.

In one embodiment, the present invention is drawn to a pharmaceutical composition comprising a compound of Formula I or II and a pharmaceutically acceptable carrier.

The compounds of Formula I or II, or a composition comprising a compound of Formula I or II, can be used for treating a variety of diseases or conditions including, but not limited to, hypertriglyceridemia, atherosclerosis, pancreatitis, obesity, hypercholesteremia, hyperchylomicronemia, hyperlipidemia, and diabetes.

Furthermore, a method for treating or preventing such a disease or condition, such as atherosclerosis and related conditions, in a subject (e.g., a mammal including a human), is provided in accordance with the present invention. The method comprises administering to a subject (e.g., a mammal including a human) in need of such a treatment, an effective amount of a compound of Formula I or II, such that the disease or condition is treated or prevented.

The present invention also provides a method of decreasing apo B secretion in a subject (e.g., a mammal or a human), comprising administering to said subject a compound of Formula I or II, or a pharmaceutical composition comprising a compound of Formula I or II, in an amount sufficient to decrease the levels or amount of secretion of apo B in the subject.

DETAILED DESCRIPTION

Figure 1:
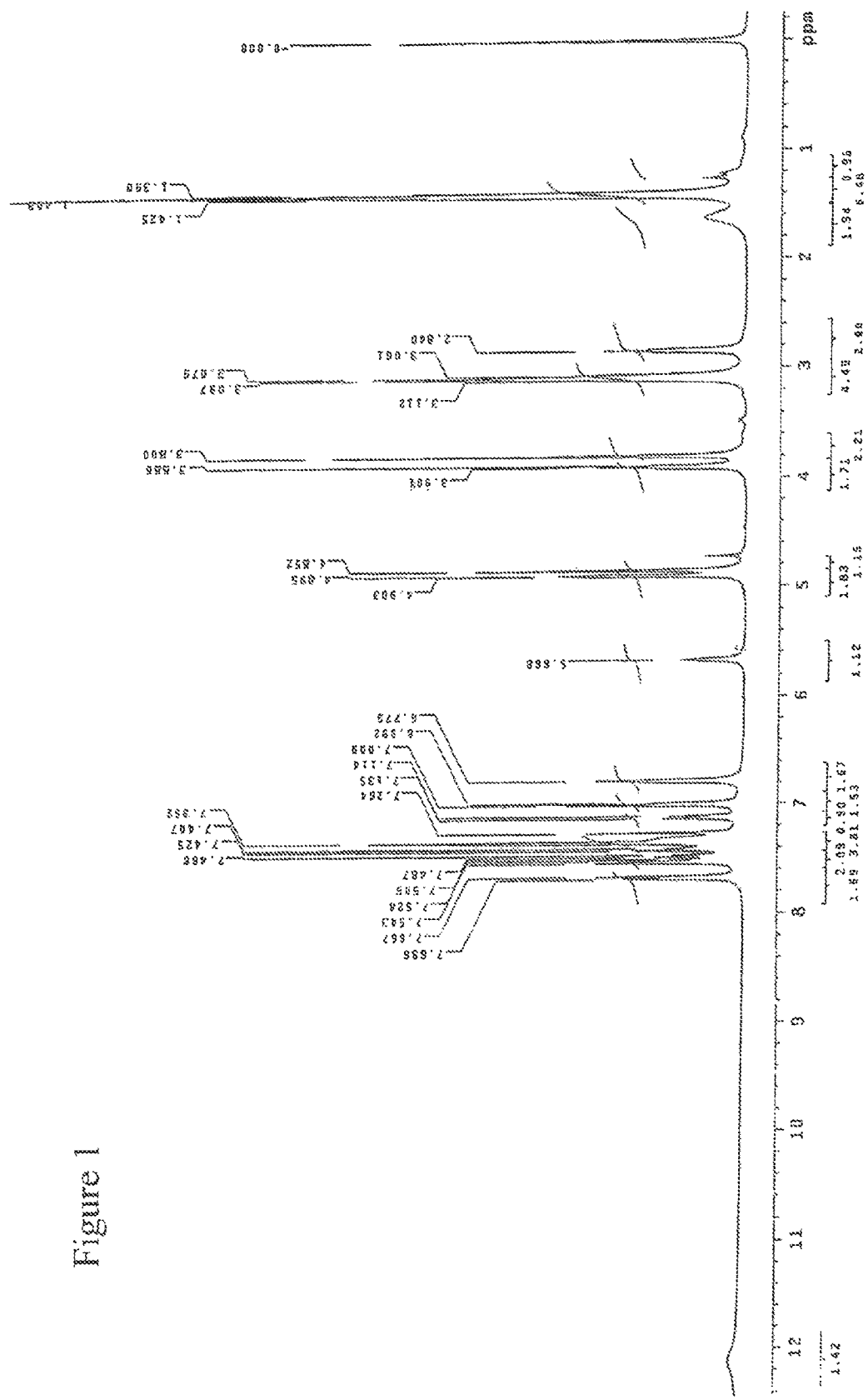
FIG. 1 is a depiction of the proton NMR of a MTP inhibitor of the present invention (compound 6).
Figure 2:
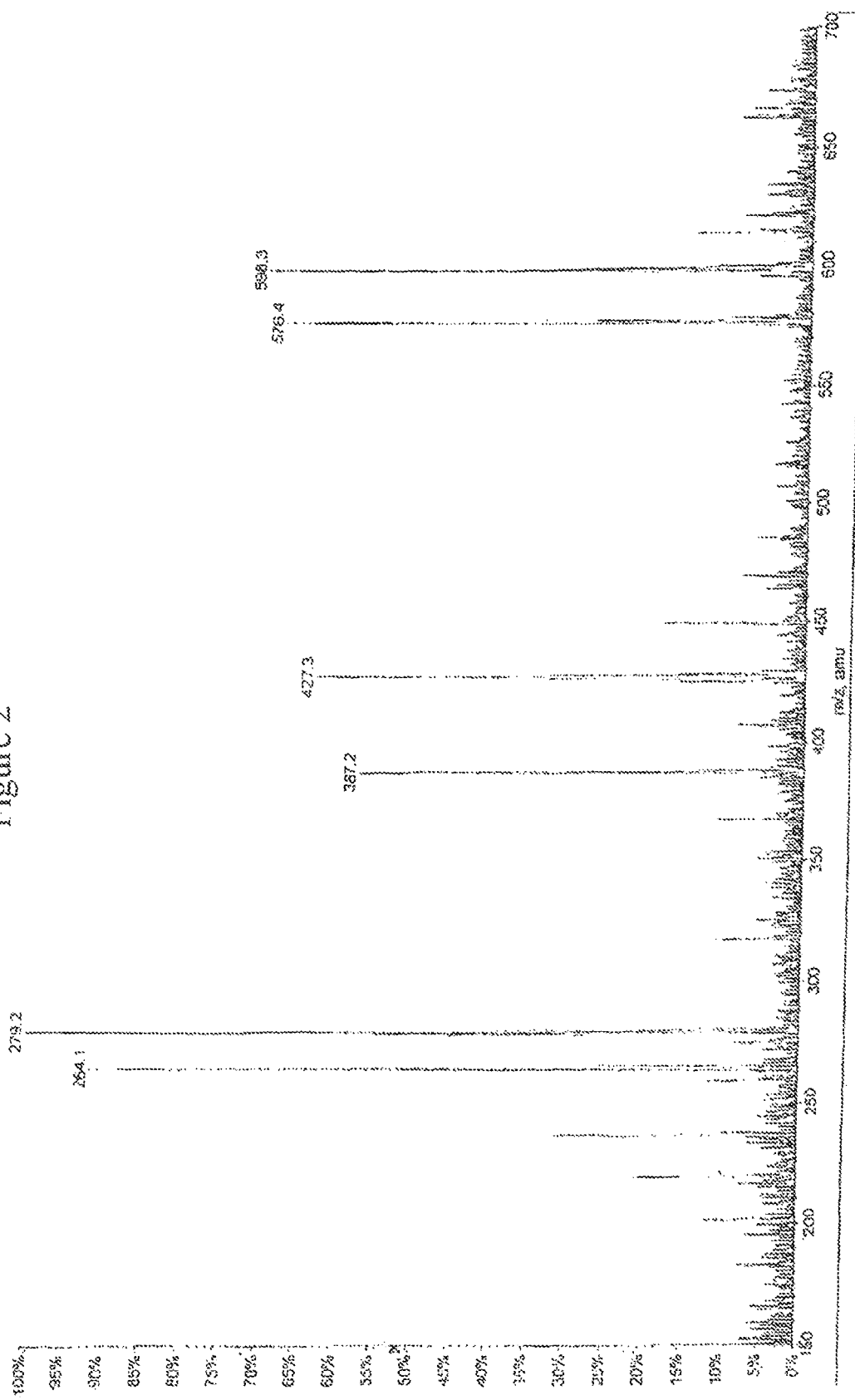
FIG. 2 is a depiction of the mass spectrum of a MTP inhibitor of the present invention (compound 6).
Figure 3:
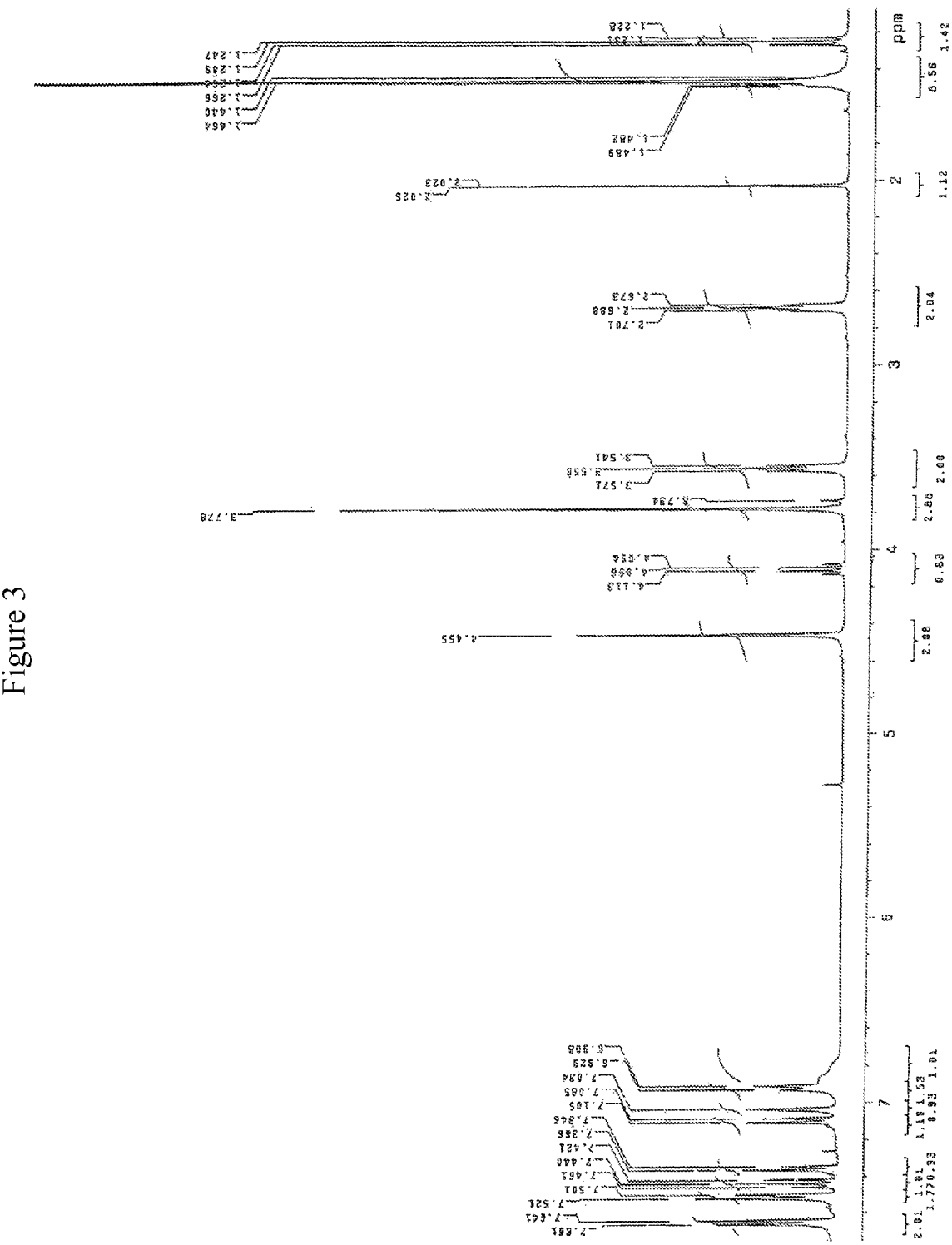
FIG. 3 is a depiction of the proton NMR of a MTP inhibitor of the present invention (compound 15).
Figure 4:
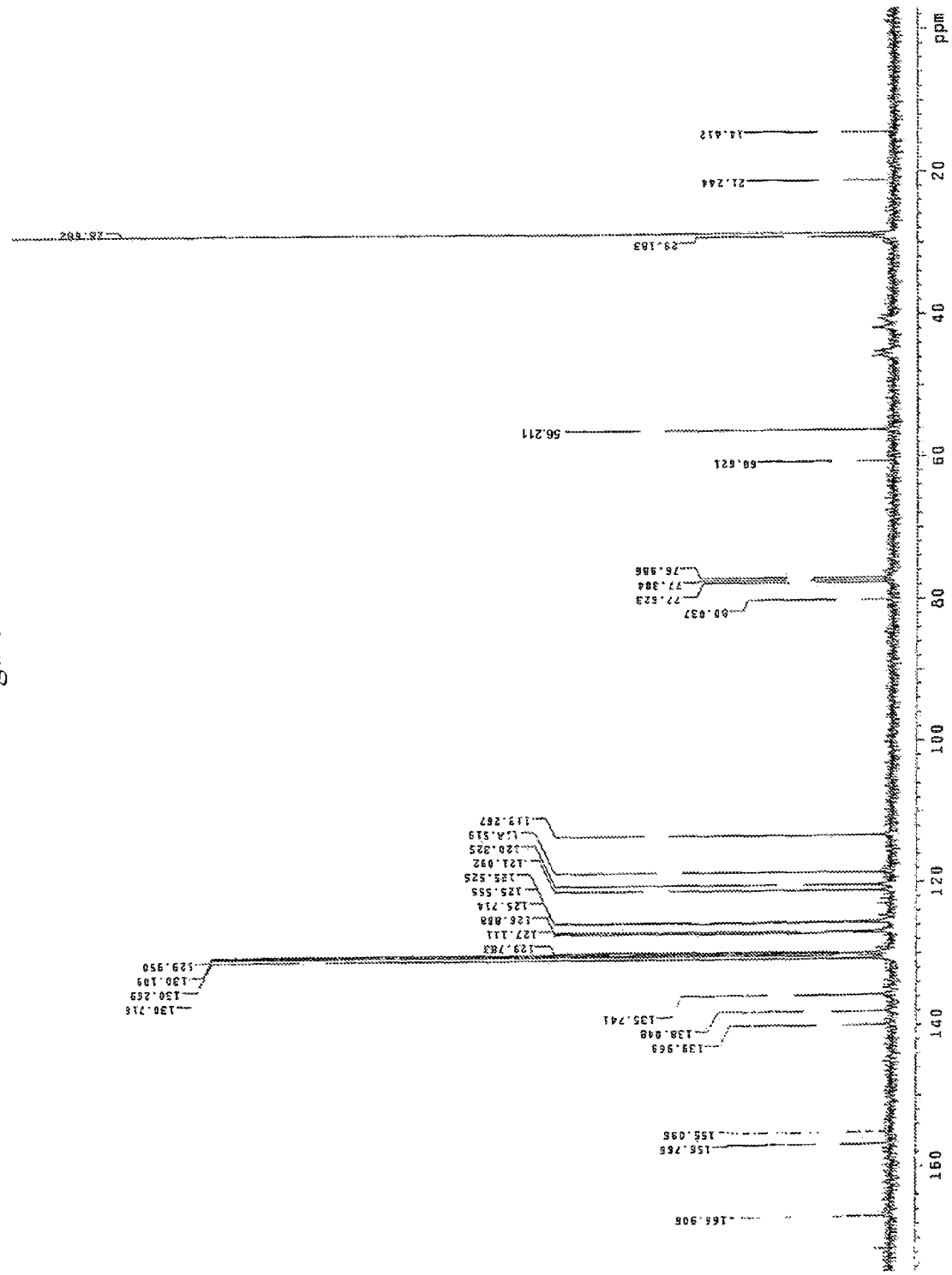
FIG. 4 is a depiction of the $^{13}$Carbon-NMR of a MTP inhibitor of the present invention (compound 15).
Figure 5:
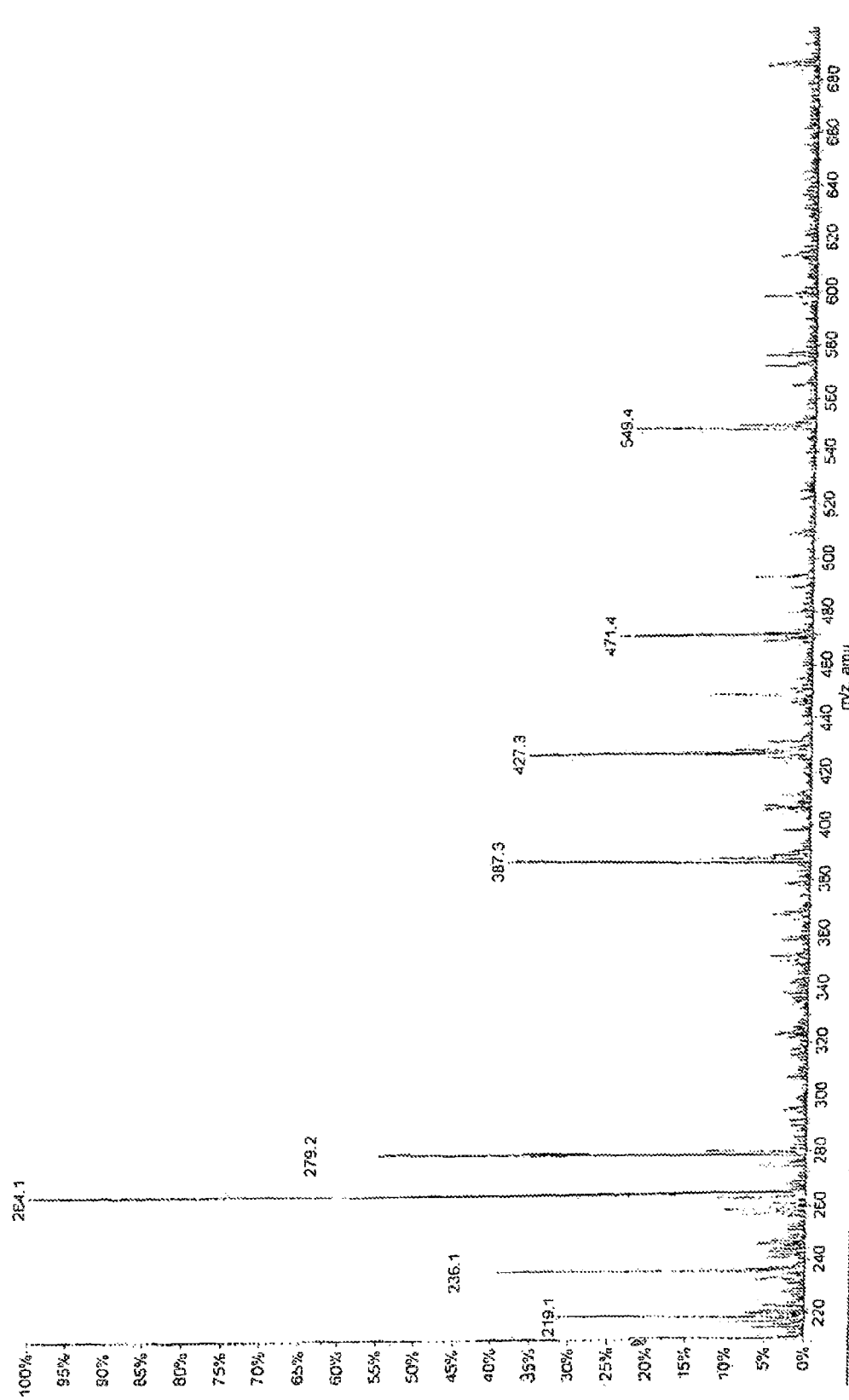
FIG. 5 is a depiction of the mass spectrum of a MTP inhibitor of the present invention (compound 15).

In one aspect, the present invention provides compounds. In one embodiment, the compounds are represented by Formula I:

(I)

wherein $R_1$ is alkyl (optionally substituted, e.g., with one to three substituents, e.g., halogen, amino, or alkoxy groups), $R_4R_5NC(O)CH_2$, cycloalkyl, heterocyclyl, or heterocyclylalkyl;

$X_1$ is a direct bond, O, S, —N($R_6$)—, C(O)N$R_6$, or N($R_6$)C(O);

$X_2$ is O, —N($R_6$)—, or S;

$X_3$ is a direct bond, O, —N($R_6$)—, —CH$_2$—, arylene, or S;

$R_3$ is H, alkyl, cycloalkyl, heterocyclyl, aryl, heteroaryl, heteroalkyl, aralkyl, alkylcarbonyl, alkoxycarbonyl, arylcarbonyl, aryloxycarbonyl, —OH, alkoxy, aryloxy, —SH, thioalkyl, thioaryl, or $NR_4R_5$;

$R_4$ and $R_5$ are, independently for each occurrence, H, alkyl, cycloalkyl, heterocyclyl, aryl, heteroaryl, heteroalkyl, aralkyl, aminocarbonyl, alkylcarbonyl, alkoxycarbonyl, arylcarbonyl, or aryloxycarbonyl;

$R_6$ is, independently for each occurrence, H or alkyl;

m is 0 or 1; and n is an integer from 0 to 3;

provided that if m is 0, $X_3$ is a direct bond or CH$_2$;

or a pharmaceutically acceptable salt, solvate, ester or hydrate thereof.

In certain preferred embodiments, $X_1$ is O. In certain preferred embodiments, $R_1$ is alkyl, more preferably methyl. In certain preferred embodiments, $R_1$ and $X_1$ taken together form a moiety selected from the group consisting of:

($C_1$-$C_6$-alkyl)-O— (e.g., $H_3C$—O—, $CH_3CH_2$—O—, $(CH_3)_2CH$—O—);

-continued most preferably, $R_1$ and $X_1$ taken together form CH$_3$—O—.

In certain preferred embodiments, m is 1. In certain preferred embodiments, when m is 1, $X_3$ is O or NH. In certain preferred embodiments, n is 0, 1 or 2. In certain preferred embodiments, $R_3$ is aryl, more preferably unsubstituted or substituted phenyl. In other preferred embodiments, $R_3$ is cycloalkyl, heterocyclyl, heteroaryl, or alkoxy. In certain preferred embodiments, the moiety represents one of the following groups:

in which Ar is optionally substituted aryl or optionally substituted heteroaryl; Cy is optionally substituted cycloalkyl or optionally substituted heterocyclyl; Alk is optionally substituted alkyl; n is 0-3; and p is 1-3. In certain preferred embodiments, n is 0 or 1. In certain preferred embodiments, Ar is optionally substituted phenyl or optionally substituted furan-2-yl; Cy is optionally substituted cyclopropyl or tetrahydrofuran-2-yl; and Alk is methyl, ethyl, or isopropyl.

In more preferred embodiments, the moiety represents one of the following groups -continued

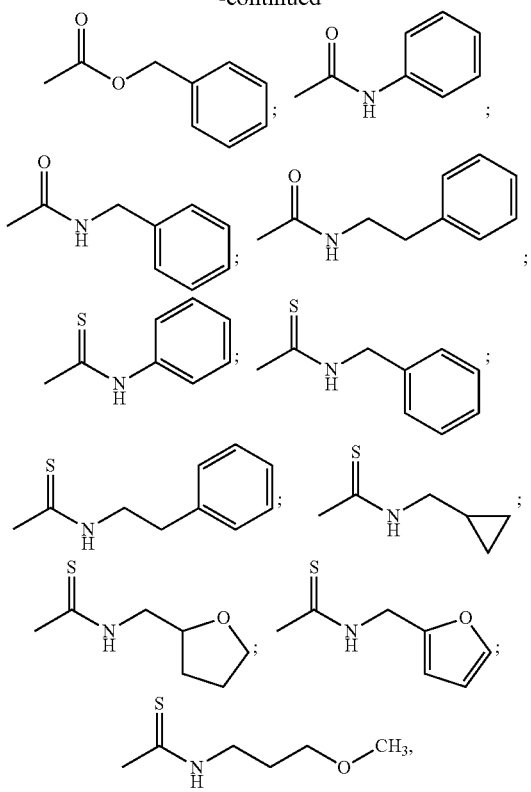

In another embodiment, the compounds are represented by Formula II

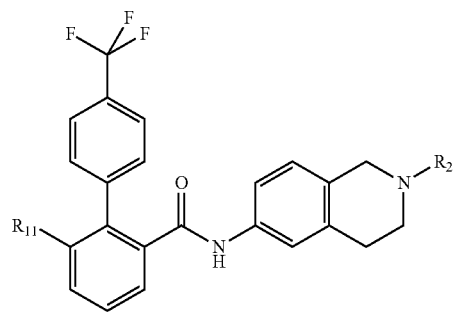
(II)

wherein $R_{11}$ is selected from:
H; $H_3C$—O—,

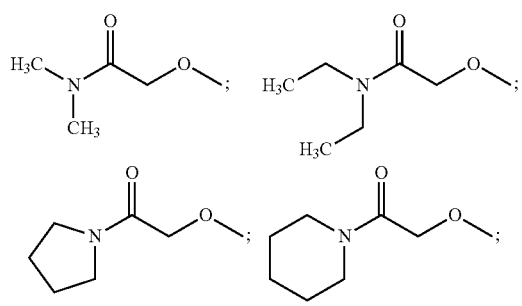

-continued

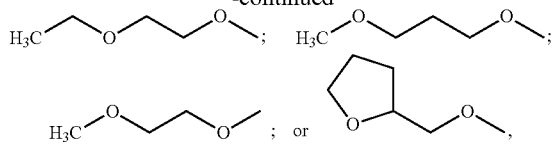

and wherein $R_{12}$ is selected from:

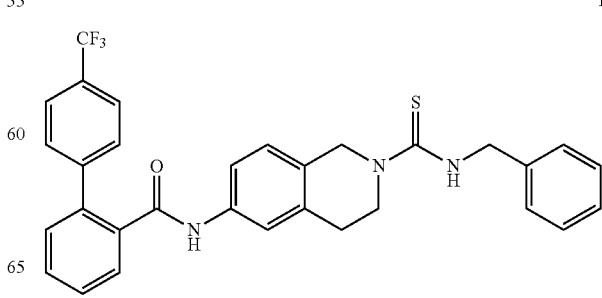

and pharmaceutically acceptable salts, esters, isomers, or hydrate thereof.

In certain preferred embodiments, $R_{11}$ is —$OCH_3$. In certain preferred embodiments, $R_{11}$ is not H.

Among the more preferred compounds of Formula I and/or II of the present invention are the following compounds:

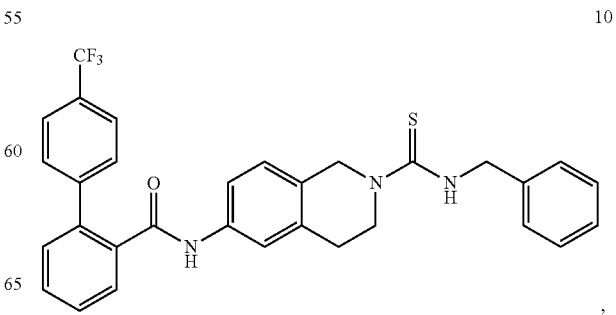

10

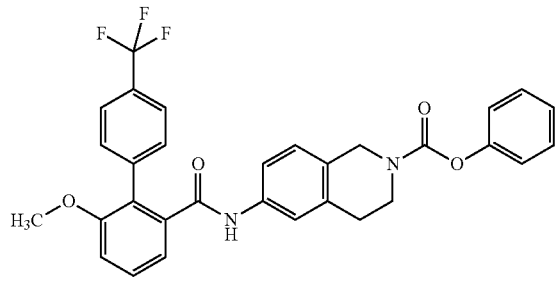

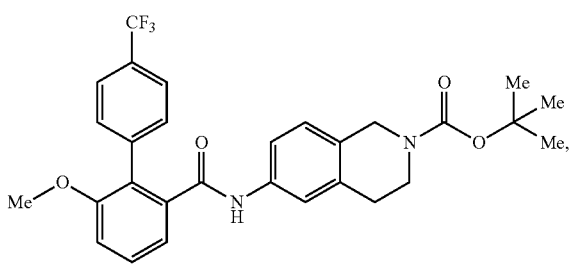

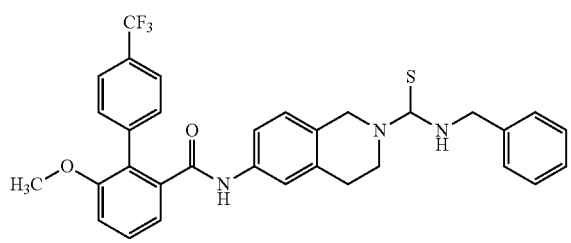

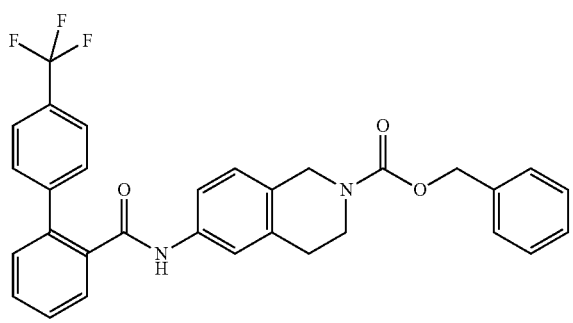

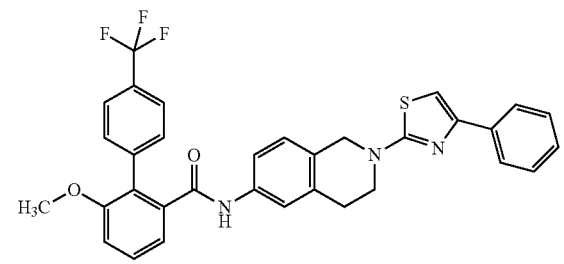

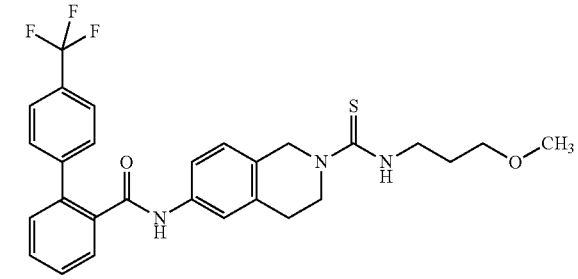

and pharmaceutically acceptable salts, esters, isomers and hydrates thereof.

As used herein, the term "alkyl" means a saturated straight chain or branched non-cyclic hydrocarbon typically having from 1 to 10 carbon atoms, more preferably from 1 to 6 carbon atoms. Representative straight chain alkyls include methyl, ethyl, n-propyl, n-butyl, n-pentyl, n-hexyl, n-heptyl, n-octyl, n-nonyl and n-decyl; branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2, 3-dimethylbutyl, 2,3-dimethylpentyl, 2, 4-dimethylpentyl, 2, 3-dimethylhexyl, 2,4-dimethylhexyl, 2, 5-dimethylhexyl, 2, 2-dimethylpentyl, 2, 2-dimethylhexyl, 3, 3-dimethylpentyl, 3, 3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3, 3-diethylhexyl, 2, 2-diethylhexyl, 3,3-diethylhexyl and the like. Alkyl groups included in compounds of this invention may be optionally substituted with one or more substituents (preferably one to three substituents), such as amino ($NH_2$), $C_1$-$C_6$ alkylamino, $C_1$-$C_6$ dialkylamino, arylamino, diarylamino, heterocyclylamino, ($C_1$-$C_6$ alkyl)carbonylamino, $C_1$-$C_6$ alkoxy, $C_1$-$C_6$ alkylthio, oxo, =S, halo (including F, Cl, Br, and I), nitro, hydroxyl, cyano, aryl, heteroaryl, aryloxy, arylthio, carbocyclyl, carbocyclyloxy, carbocyclylthio, carbocyclylamino, heterocyclyl, heterocyclyloxy, heterocyclylthio, and the like. Lower alkyls (having from 1 to 6 carbon atoms in the alkyl chain) are typically preferred for the compounds of this invention.

The term "cycloalkyl", as used herein, refers to a cyclic alkyl group having from 3 to 10 carbon atoms in the ring, more preferably 3-6 carbon atoms in the ring. Exemplary cycloalkyl groups include cyclopropyl, cyclobutyl, cyclopentyl, and cyclohexyl. Cycloalkyls may be substituted by one or more substituents (e.g., one to three substituents) as described above for alkyl groups.

As used herein, the term "heterocycle" or "heterocyclyl" means a monocyclic or polycyclic heterocyclic ring (typically having 3- to 14-members) which is either a saturated ring or a unsaturated non-aromatic ring. A 3-membered heterocycle can contain up to 3 heteroatoms, and a 4- to 14-membered heterocycle can contain from 1 to about 8 heteroatoms. Each heteroatom is independently selected from nitrogen, which can be quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents, e.g., one to three substituents (including without limitation a halogen atom, an alkyl radical, or aryl radical). Only stable isomers of such substituted heterocyclic groups are contemplated in this definition. Heterocyclyl groups can be substituted or unsubstituted.

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or, optionally, substituted with one or more substituents, e.g., one to three substituents (including without limitation alkyl (preferably, lower alkyl or alkyl substituted with one or more halo), hydroxy, alkoxy (preferably, lower alkoxy), alkylthio, cyano, halo, amino, and nitro. In certain embodiments, the aryl group is a monocyclic ring, wherein the ring comprises 6 carbon atoms.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur and nitrogen. In another embodiment, the heteroaromatic ring is a 5- or 6-membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl and the like. These heteroaryl groups may be optionally substituted with one or more substituents, e.g., one to three substituents as described for aryl groups.

As used herein, the term "halogen" or "halo" means —F, —Cl, —Br or —I.

The term "alkylene," as used herein, refers to an alkyl group that has two points of attachment to two moieties (e.g., {—CH$_2$—}, —{CH$_2$CH$_2$—},

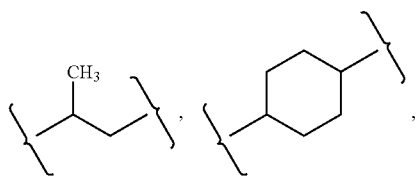

etc., wherein the brackets indicate the points of attachment). Alkylene groups may be unsubstituted or optionally substituted with one or more substituents, e.g., 1-3 substituents as described for alkyl groups. Exemplary alkylene groups include methylene, ethylene, and propylene.

The term "arylene," as used herein, refers to an aryl or heteroaryl group that has two points of attachment to two moieties. Arylene groups may be unsubstituted or optionally substituted with one or more substituents, e.g., 1-3 substituents as described for alkyl groups. Exemplary arylene groups include phenyl-1,2-diyl, phenyl-1,3-diyl, and phenyl-1,4-diyl-; thiazol-2,4-diyl, and the like.

The term "aralkyl", as used herein, refers to an aryl group that is attached to another moiety via an alkylene linker. Aralkyl groups may be unsubstituted or optionally substituted with one or more substituents, e.g., 1-3 substituents as described for alkyl groups.

The term "heterocyclylalkyl," as used herein, refers to a heterocyclyl group that is attached to another moiety via an alkylene linker. Heterocyclylalkyl groups may be unsubstituted or optionally substituted with one or more substituents, e.g., 1-3 substituents as described for alkyl groups.

The term "alkylcarbonyl," as used herein, refers to the group —C(O)-alkyl. The alkyl portion of the alkylcarbonyl moiety can be unsubstituted or optionally substituted with one or more substituents, e.g., 1-3 substituents as described above for alkyl groups.

The term "alkoxycarbonyl," as used herein, refers to the group —C(O)—O-alkyl. The alkyl portion of the alkoxycarbonyl moiety can be unsubstituted or optionally substituted with one or more substituents, e.g., 1-3 substituents as described above for alkyl groups.

The term "arylcarbonyl," as used herein, refers to the group —C(O)-aryl or —C(O)-heteroaryl. The aryl or heteroaryl portion of the arylcarbonyl moiety can be unsubstituted or optionally substituted with one or more substituents, e.g., 1-3 substituents as described above for alkyl groups.

The term "aryloxycarbonyl," as used herein, refers to the group —C(O)—O-aryl or —C(O)—O— heteroaryl. The aryl or heteroaryl portion of the aryloxycarbonyl moiety can be unsubstituted or optionally substituted with one or more substituents, e.g., 1-3 substituents as described above for alkyl groups.

The term "aminocarbonyl," as used herein, refers to the groups —C(O)—NR$_a$R$_b$, in which R$_a$ and R$_b$ are independently H, alkyl, aryl, heteroaryl, cycloalkyl, or heterocyclyl. The alkyl, aryl, heteroaryl, cycloalkyl, or heterocyclyl portion of the aminocarbonyl moiety can be unsubstituted or optionally substituted with one or more substituents, e.g., 1-3 substituents as described above for alkyl groups.

The term "alkoxy," as used herein, refers to the group —O-alkyl. The alkyl portion of the alkoxy moiety can be unsubstituted or optionally substituted with one or more substituents, e.g., 1-3 substituents as described above for alkyl groups.

The term "aryloxy," as used herein, refers to the group —O-aryl or —O-heteroaryl. The aryl or heteroaryl portion of the aryloxy moiety can be unsubstituted or optionally substituted with one or more substituents, e.g., 1-3 substituents as described above for alkyl groups.

The term "thioalkoxy," as used herein, refers to the group —S-alkyl. The alkyl portion of the thioalkoxy moiety can be unsubstituted or optionally substituted with one or more substituents, e.g., 1-3 substituents as described above for alkyl groups.

The term "thioaryloxy," as used herein, refers to the group —S-aryl or —S-heteroaryl. The aryl or heteroaryl portion of the thioaryloxy moiety can be unsubstituted or optionally substituted with one or more substituents, e.g., 1-3 substituents as described above for alkyl groups.

In another aspect, the present invention provides pharmaceutical compositions comprising a compound of Formula I or II and a pharmaceutically acceptable carrier.

The compounds of Formula I or II or compositions comprising the compounds of Formula I or II can be used for treating a variety of diseases or conditions including, but not limited to, atherosclerosis, pancreatitis, obesity, hypercholesteremia, hypertriglyceridemia, hyperlipidemia, and diabetes.

Furthermore, a method for treating such a disease or condition, such as atherosclerosis and related conditions, in a mammal or a human, is provided in accordance with the present invention. The method comprises administering to a subject (e.g., a mammal, including a human) in need of such a treatment an effective amount of a compound of Formula I or II, or a pharmaceutical composition comprising an effective amount of a compound of Formula I or II, such that the disease or condition is treated. In certain embodiments, the compound is administered in an amount sufficient to decrease the secretion of apolipoprotein B.

The present invention also provides for a method of decreasing apo B secretion in a mammal or human, comprising administering to a mammal or a human of a compound of Formula I or II, or a pharmaceutical composition comprising a compound of Formula I or II, in an amount sufficient to decrease the levels or amount of secretion of apo B.

The invention further provides a pharmaceutical composition suitable for the treatment of conditions including hypertriglyceridemia, atherosclerosis, pancreatitis, obesity, hypercholesterolemia, hyperchylomicronemia, hyperlipidemia, and diabetes, comprising a compound of Formula I or II as hereinbefore defined, and a pharmaceutically acceptable carrier.

The compounds of this invention inhibit or decrease apo B secretion, likely by the inhibition of MTP, although it may be possible that other mechanisms are involved as well. The compounds are useful in any of the diseases or conditions in which apo B, serum cholesterol, and/or triglyceride levels are elevated. Accordingly, the invention further provides a method of treating a condition selected from hypertriglyceridemia, atherosclerosis, pancreatitis, obesity, hypercholesteremia, hyperchylomicronemia, hyperlipidemia, and diabetes, comprising administering to a mammal, especially a human, in need of such treatment an amount of a compound of Formula I or II as defined above sufficient to decrease the secretion of apolipoprotein B.

The term "treating" as used herein includes preventative as well as disease remitative treatment.

The invention further provides a method of decreasing apo B secretion in a mammal, especially a human, comprising administering to said mammal an apo B-(secretion) decreasing amount of a compound of Formula I or II as defined above.

The invention also provides kits for treatment or prevention of diseases or conditions in which apo B, serum cholesterol, and/or triglyceride levels are elevated. Accordingly, the invention further provides kits for treatment or prevention of a condition selected from hypertriglyceridemia, atherosclerosis, pancreatitis, obesity, hypercholesteremia, hyperchylomicronemia, hyperlipidemia, and diabetes. In one embodiment, the kit includes an effective amount of a compound of this invention (e.g., a compound of Formula I or Formula II) in unit dosage form, together with instructions for administering the compound to a subject suffering from or susceptible to diseases or conditions in which apo B, serum cholesterol, and/or triglyceride levels are elevated (including without limitation hypertriglyceridemia, atherosclerosis, pancreatitis, obesity, hypercholesteremia, hyperchylomicronemia, hyperlipidemia, and diabetes), preferably wherein the effective amount of compound is less than 1000 mg (more preferably less than 500 mg) of the compound.

In preferred embodiments, the kit comprises a sterile container which contains the compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments.

The instructions will generally include information about the use of the compound for treatment or prevention of diseases or conditions in which apo B, serum cholesterol, and/or triglyceride levels are elevated (including without limitation hypertriglyceridemia, atherosclerosis, pancreatitis, obesity, hypercholesteremia, hyperchylomicronemia, hyperlipidemia, and diabetes); in preferred embodiments, the instructions include at least one of the following: description of the compound; dosage schedule and administration for treatment of diseases or conditions in which apo B, serum cholesterol, and/or triglyceride levels are elevated; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

In another aspect, the present invention provides intermediate compounds that are useful for the synthesis of the MTP inhibitor compounds of the invention. Examples of such intermediate compounds include compounds of structure 20, in which R$_1$ and X$_1$ have the meanings described in connection with Formula I or II, and R$_7$ is selected from the group consisting of OH, O-Cat (in which Cat is a cation (e.g., a proton, a metal cation such as sodium, lithium, potassium, calcium, ammonium, and the like)), a C$_1$-C$_6$ alkoxy group, and a leaving group (including a halogen such as chloride or bromide, a tosylate or mesylate, a pentafluorophenol, and the like).

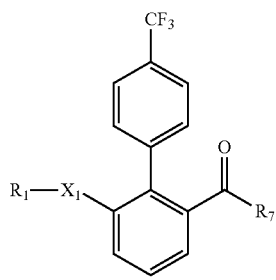

20

In a preferred embodiment of a compound of structure 20, $R_1$ together with $X_1$ forms a $CH_3O$ group, and $R_7$=OH.

The present invention also provides intermediates useful in the preparation of compounds of Formula I or Formula II. A preferred intermediate compound of the present invention is described by structure 2 shown below.

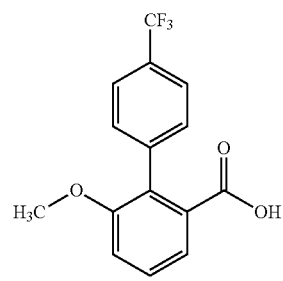

2

It will be appreciated by those skilled in the art that certain compounds of Formula I or II may contain an asymmetrically substituted carbon atom and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of atherosclerosis, obesity, and the other conditions noted herein, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the conditions noted herein by the standard tests described hereinafter.

The chemist of ordinary skill will recognize that certain combinations of substituents or moieties listed in this invention define compounds which will be less stable under physiological conditions (e.g., those containing aminal or acetal linkages). Accordingly, such compounds are less preferred.

The present invention further provides a method of forming the compounds of Formula I or II of the present invention by a synthetic process. Compounds of Formula I or II can also be made by processes which include processes known in the chemical arts for the production of similar compounds. Such processes for the manufacture of a compound of Formula I or II as defined above are provided as further features of the invention and are illustrated by the procedures discussed below.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-liquid) extraction techniques.

The compounds herein form cationic salts such as acid addition salts and the expression "pharmaceutically-acceptable salts" is intended to define but not be limited to such salts as the hydrochloride, hydrobromide, sulfate, hydrogen sulfate, phosphate, hydrogen phosphate, dihydrogenphosphate, acetate, succinate, citrate, benzoate, ascorbate, lactate, pamoate, tartrate, methanesulfonate (mesylate) and p-toluenesulfonate (tosylate) salts. For many compounds polyaddition salts are feasible.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

In certain embodiments, the term "pharmaceutically acceptable salt," as used herein, can refer to a salt prepared from a compound of Formula I or II having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like.

A representative general synthetic route for the MTP inhibitor compounds of Formula I or II of the present invention is exemplified in Scheme 1, which shows the synthesis of compound 6. The individual reaction steps involved in the synthetic process are subsequently described in greater detail (see Examples 1-7).

Scheme 1

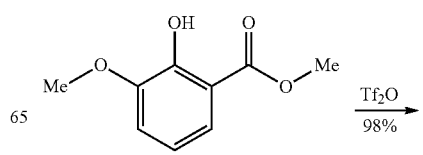

-continued
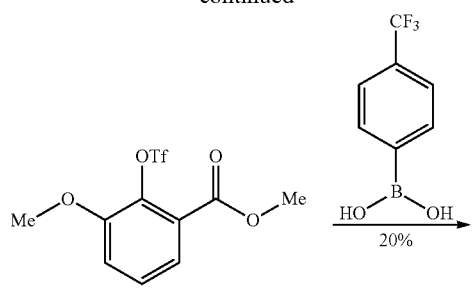
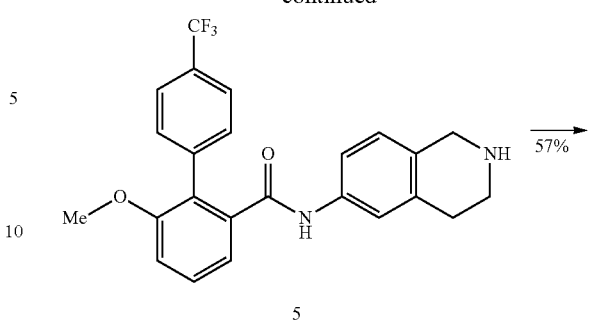
5
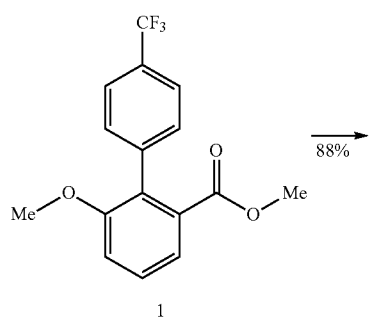
1
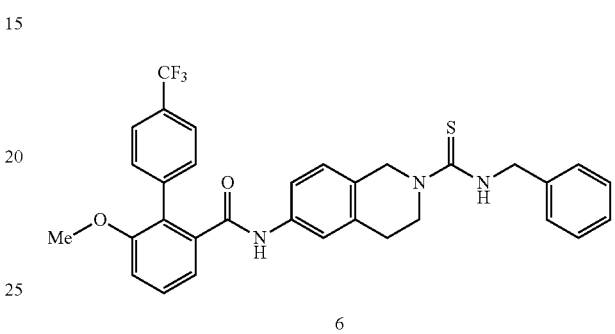
6
Step 1: From Alcohol to Triflate
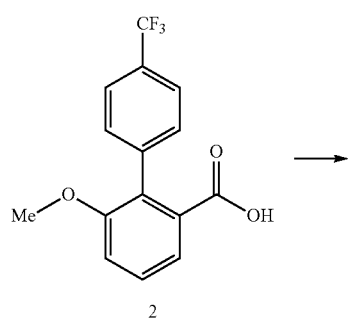
2
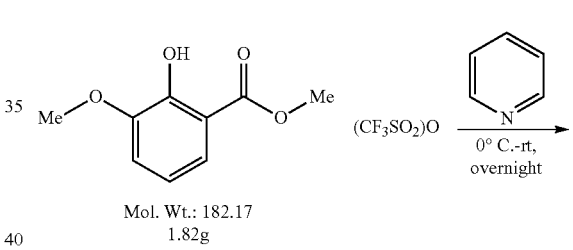
Mol. Wt.: 182.17
1.82g
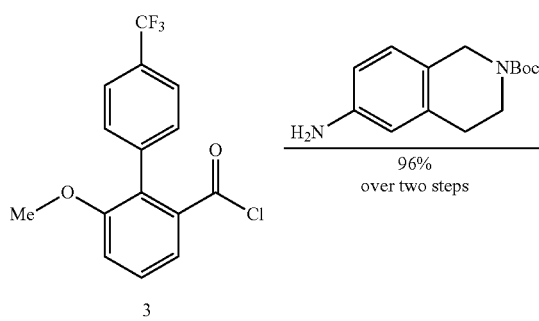
3
Mol. Wt.: 314.24
yield = 98%
Step 2: Aromatic Coupling (Suzuki Coupling)
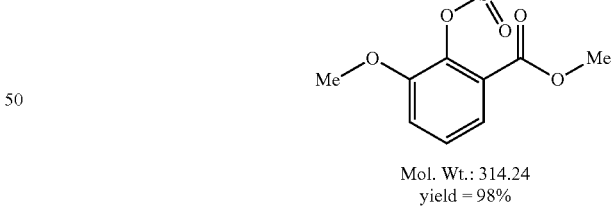
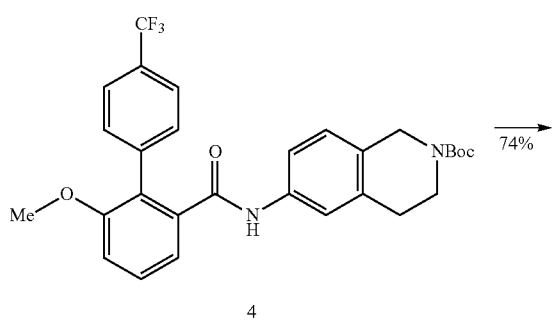
4
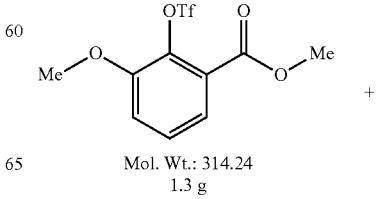
Mol. Wt.: 314.24
1.3 g 21
-continued
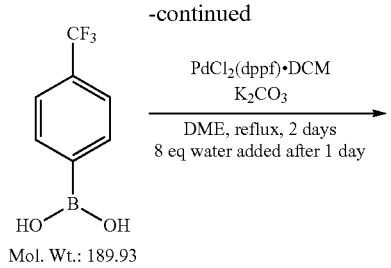
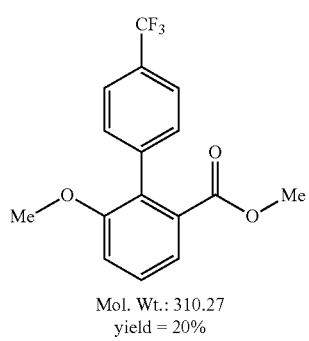
Mol. Wt.: 310.27
yield = 20%
Step 3: Deprotection of Ester
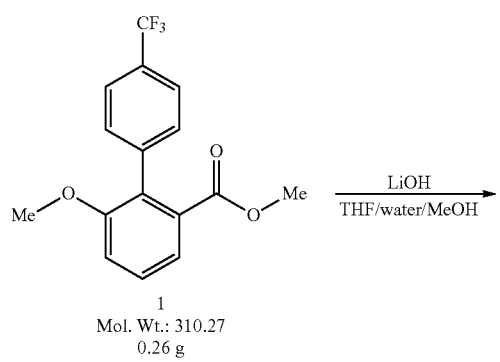
Step 4: Formation of Acyl Chloride
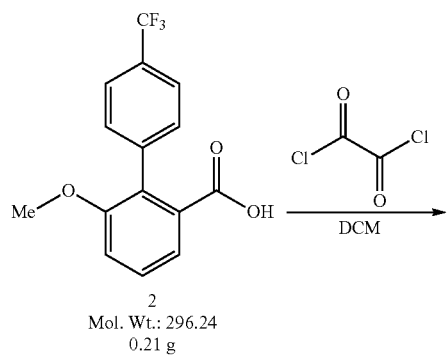
22
-continued
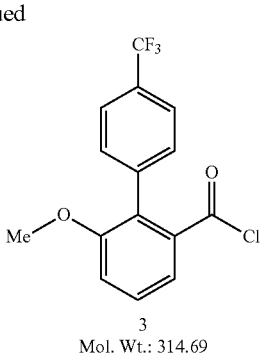
3
Mol. Wt.: 314.69
Step 5: Coupling with N-Boc Tetrahydroisoquinoline
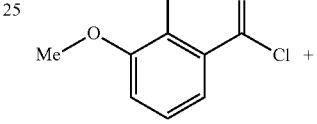
3
+
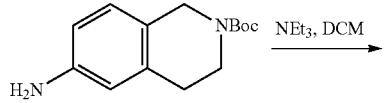
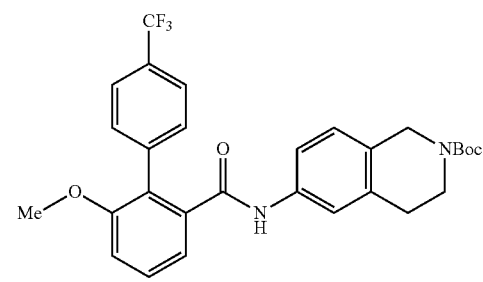
4
yield = 96%
Step 6: Removal of Boc Protecting Group.
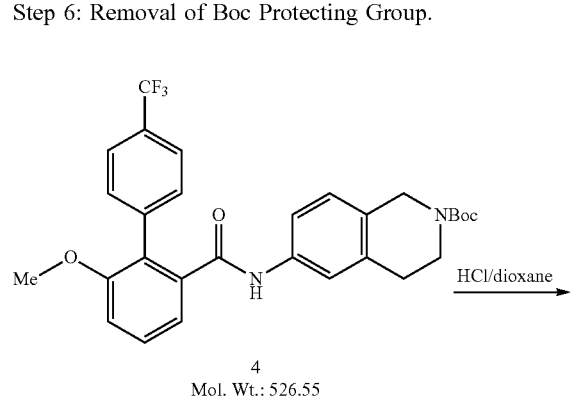
4
Mol. Wt.: 526.55

-continued

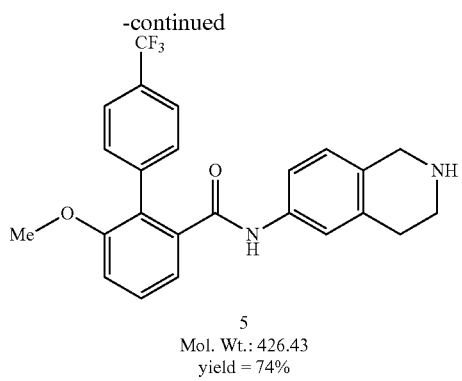

5
Mol. Wt.: 426.43
yield = 74%

Step 7: Formation of Thiourea

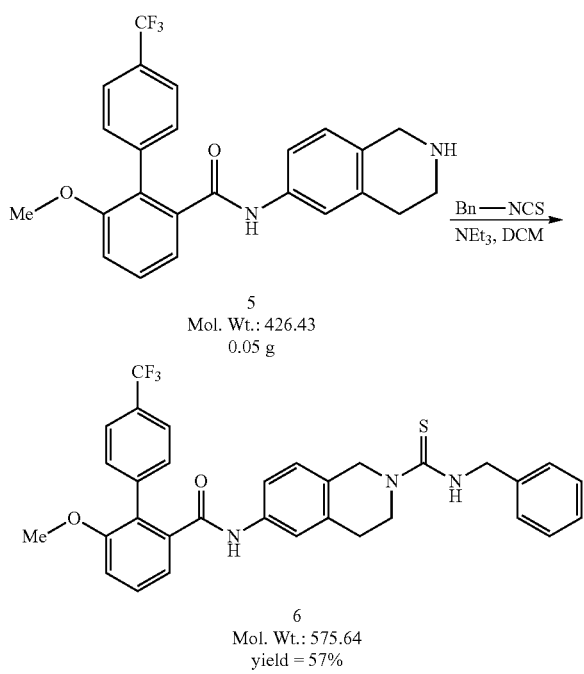

6
Mol. Wt.: 575.64
yield = 57%

The compounds of the present invention are orally administrable and are accordingly used in combination with a pharmaceutically acceptable carrier or diluent suitable to oral dosage forms. Suitable pharmaceutically-acceptable carriers include inert solid fillers or diluents and sterile aqueous or organic solutions. The active compound will be present in such pharmaceutical compositions in amounts sufficient to provide the desired dosage amount in the range described below. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. For parenteral administration the compounds can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syingability exists. It must be stable under the conditions of manufacture and storage and must be preserved against the contaminating action of microorganisms such as bacteria and fungi.

The dose of a compound of Formula I or II which is administered will generally be varied according to principles well known in the art taking into account the severity of the condition being treated and the route of administration. In general, a compound of Formula I or II will be administered to a warm blooded animal (such as a human) so that an effective dose, usually a daily dose administered in unitary or divided portions, is received, for example a dose in the range of about 0.1 to about 15 mg/kg body weight, preferably about 1 to about 5 mg/kg body weight. The total daily dose received will generally be between 1 and 1200 mg, preferably between 5 and 800 mg. In certain preferred embodiments, a compound of Formula I or II may be administered in divided doses taken with meals, e.g., three times daily, in which case each dose can be, e.g., between 5 and 500 mg.

The compounds of this invention may be used in conjunction with other pharmaceutical agents, including other lipid lowering agents. Such agents include cholesterol biosynthesis inhibitors, especially HMG CoA reductase inhibitors (such as atorvastatin, pravastatin, simvastatin, lovastatin, fluvastatin, cerivastatin, rosuvastatin, and pitivastatin (itavastatin/risivastatin)); squalene synthetase inhibitors; bile acid sequestrants such as cholestyramine; fibrates (bezafibrate, clofibrate, fenofibrate); cholesterol absorption inhibitors such as ezetimibe and pamaqueside; and niacin.

A test compound is considered to be active if it is active in any of the following screens. The activity of a compound according to the invention can be assessed by measuring inhibition of apo B secretion in HepG2 cells.

Activity can also be confirmed if a test compound inhibits MTP activity directly. Inhibition of MTP activity by a compound can be quantitated by observing the inhibition of transfer of radiolabeled triglyceride from donor vesicles to acceptor vesicles in the presence of soluble human MTP.

The present invention is illustrated by the following Examples. However, it should be understood that the invention is not limited to the specific details of these examples.

EXAMPLES

Example 1

Formation of Triflate from Alcohol

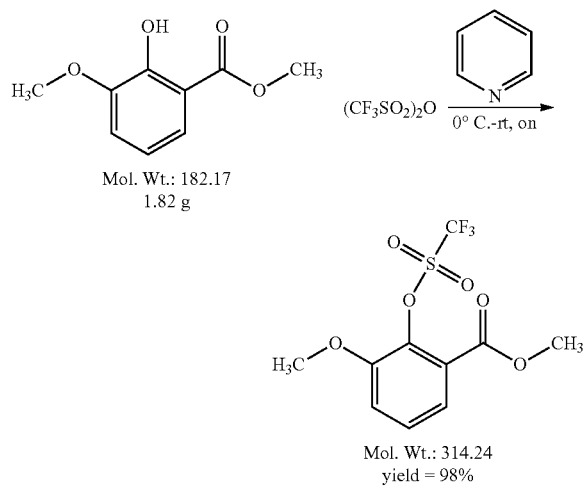

A mixture of phenol (1.82 g) and trifluoromethanesulfonyl (1.05 eq) anhydride in anhydrous pyridine (1M) was stirred at 0° C. and then slowly warmed up to 15° C. overnight. Water was added to the mixture, which then was extracted three times with Et₂O. The organic layer was washed with brine and dried over Na₂SO₄. The solvent was removed under reduced pressure and the crude was passed through a plug of silica gel to afford 3.07 g (98%) of the triflate (purity 98%).

Example 2

Aromatic Coupling (Suzuki Coupling)

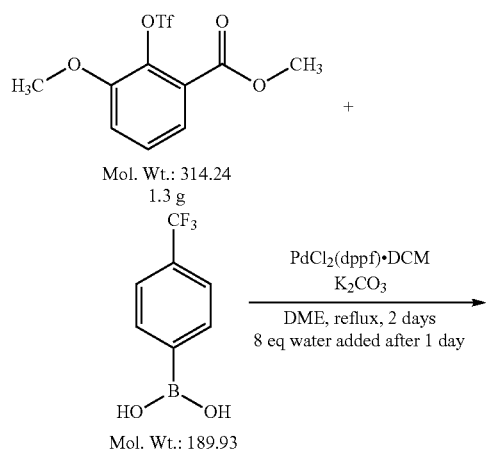

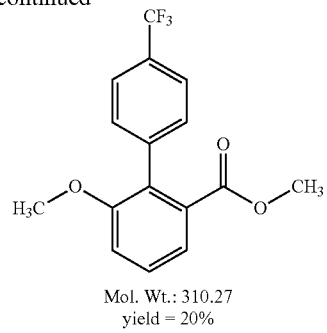

Mol. Wt.: 310.27
yield = 20%

The triflate (1.3 g) was dissolved in 25 mL of DME (0.16M) and the boronic acid (0.64 g, 0.8 eq), K₂CO₃ (0.85 g, 1.49 mmol) and PdCl₂dppf-DCM (0.02 eq) were added. The mixture was refluxed over night. In the morning all the reagents were added to reach 1.05 eq of boronic acid, 2.0 eq of K₂CO₃ and 0.03 eq of catalyst. The mixture was heated for additional 5 hours, and then water (8.0 eq) was added. After 18 hours, the reaction mixture was diluted with Et₂O, and it was filtered through a silica gel plug column and eluted with Et₂O. No separation of impurities from product occurred. The organic phase was washed with a solution of citric acid (10%), 2×brine and dried over Na₂SO₄. The solvent was removed under reduced pressure. The residue was dissolved in MeOH, water was added and some precipitate was formed. The solid was collected, washed with hexanes, dissolved in DCM and crystallized again with hexanes. The solid was isolated (0.26 g, pure 97.5% by HPLC)

Example 3

Deprotection of Ester

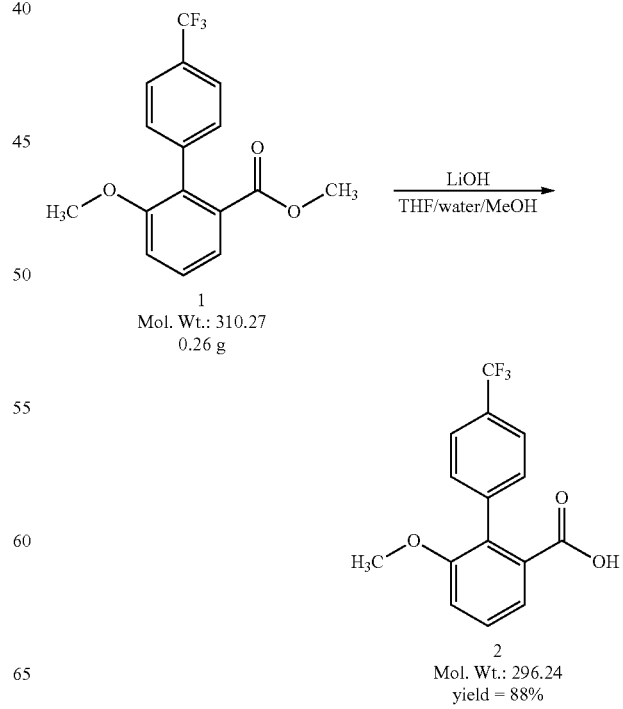

Compound 1 (0.26 g) was dissolved in THF (2.0 mL) and LiOH.H₂O (4.8 eq) was added in 1.0 mL of water. After stirring the mixture at room temp, MeOH was added to have a homogenous solution. The mixture was heated at 50° C. overnight. The solvent was removed under reduced pressure, the residue was dissolved in DCM and washed with 1N HCl and brine. The organic phase was dried over Na₂SO₄ and the removal of the solvent by reduced pressure afforded 0.22 g (88%) of compound 2 (purity 98%).

Example 4

Formation of Acyl Chloride

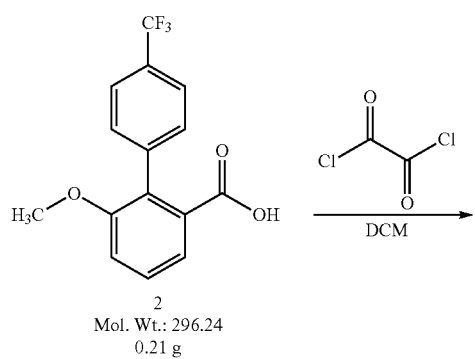

2
Mol. Wt.: 296.24
0.21 g

3
Mol. Wt.: 314.69

Compound 2 (0.21 g) was suspended in DCM (3.0 mL) and the solution was cooled to 0° C. Oxalyl chloride (1.6 eq) was added dropwise followed by the addition of catalytic amount of DMF. The mixture was stirred at 0° C. for 30 minutes, then at room temperature for 1.5 hours. The solution became clear. The solvent was removed under reduced pressure. The crude was used from the next reaction without further purification.

Example 5

Coupling with N-Boc Tetrahydroisoquinoline

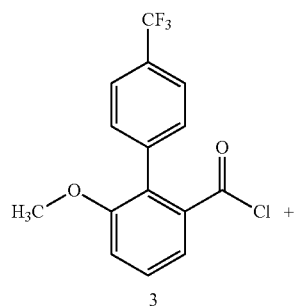

3

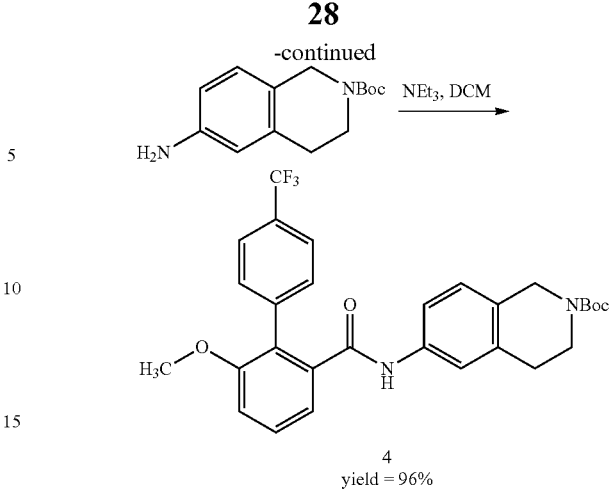

4
yield = 96%

Compound 3 was dissolved in THF (2.0 mL) and a solution of N-Boc-tetrahydroisoquinoline in 2.0 mL of THF was added dropwise (some precipitate formed) followed by the addition of NEt₃. The mixture was stirred at room temperature for 18 hours. The solvent was removed under reduced pressure and the crude was purified through silica gel column chromatography (EtOAc/Hexanes 0-30%). The product was not clean at this point. The product was washed with Et₂O to give (0.36 g) of compound 4 (purity 99%).

Example 6

Removal of Boc Protecting Group

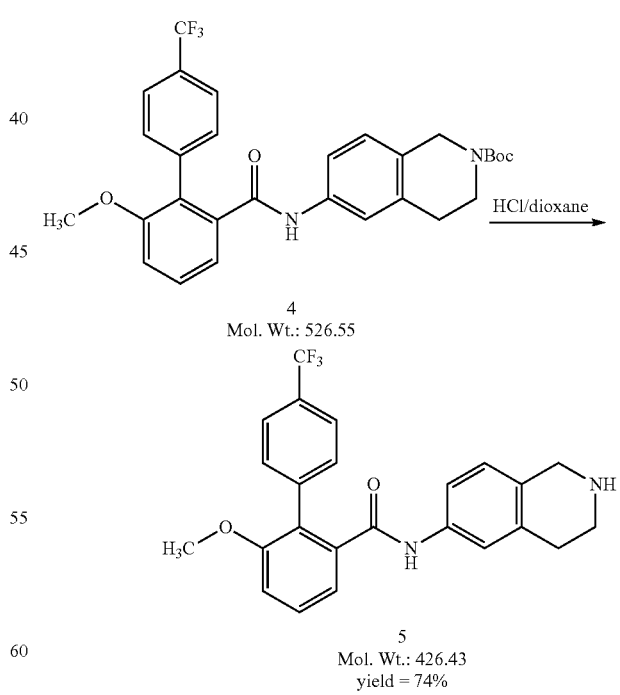

4
Mol. Wt.: 526.55

5
Mol. Wt.: 426.43
yield = 74%

Compound 4 (0.1 g) was dissolved in 4MHCl.dioxane (1.0 mL) and the solution was stirred at room temp for 2 hours. The solvent was removed under reduced pressure, the residue was dissolved in DCM and Et₂O was added. Some precipitate formed, it was filtered and wash with Et$_2$O to afford 60 mg (74%) of compound 5 (purity 95%).

Example 7

Formation of Thiourea

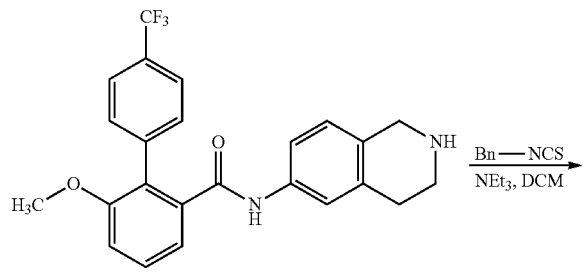

5
Mol. Wt.: 426.43
0.05 g

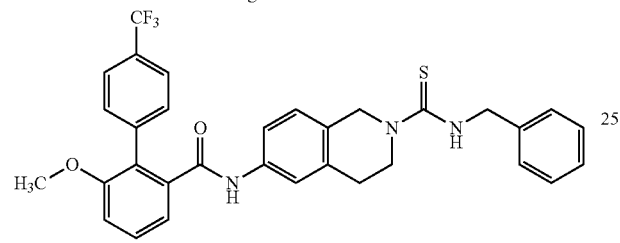

6
Mol. Wt.: 575.64
yield = 57%

Compound 5 (0.05 g) was suspended in DCM (1.5 mL) and 0.1 mL of NEt$_3$ was added. The solution became homogeneous. The mixture was stirred for 12 hours at room temperature and some precipitate was formed. Et2O was added and some additional precipitate was formed. After filtration, 38 mg (57%) of compound 6 were collected (purity 99%).

Example 8

Experimental Protocol for Apo-B/ApoA1 Assay

The following protocol is written for HepG2 cells types, but the same or similar protocol may be used with other cell types, such as Caco-2 cells.

HepG2 cells were grown in MEM Eagle's medium containing 10% fetal bovine serum with 1% penicillin/streptomycin in an incubator (5% CO$_2$, 100% relative humidity, 37° C.). At ca. 85% confluency, the cells were treated with test compounds (0.2% DMSO) at appropriate concentrations in triplicate. After 24 hour incubation with the test compounds, growth media were collected from each sample. Concentrations for apo-B and apoA1 were determined using ELISA. Mouse anti-human Apo-B and ApoA1 antibody and Alk-phos conjugated secondary antibody (goat) was used in ELISA. Triplicate data in six half-log concentrations were used to calculate an IC$_{50}$ value for each compound.

Cellular Activity

The following table (Table 1) depicts the activity of several compounds of Formula I or II according to the present invention. Permeability was measured in a bidirectional Caco-2 assay with analysis by fluorescence and HPLC.

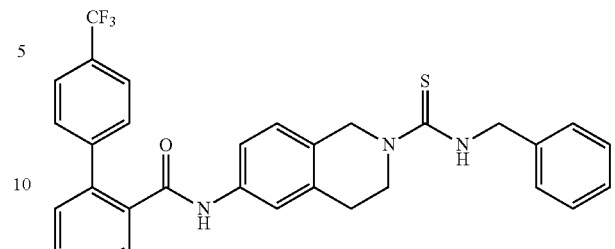

10

11

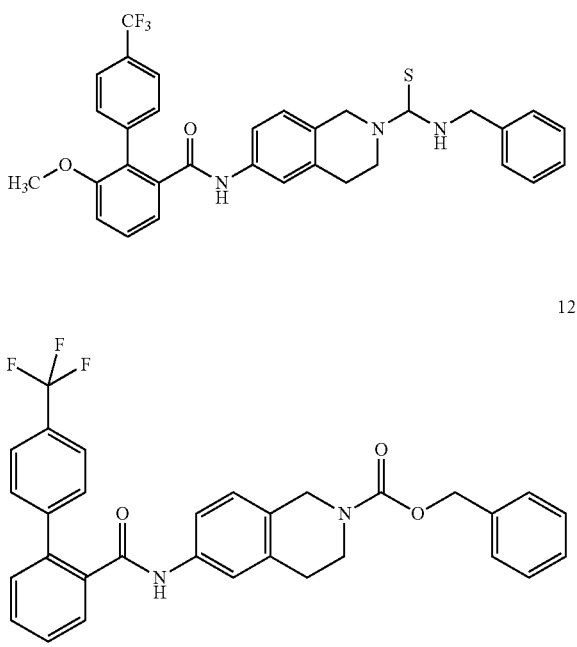

15

6

12

-continued

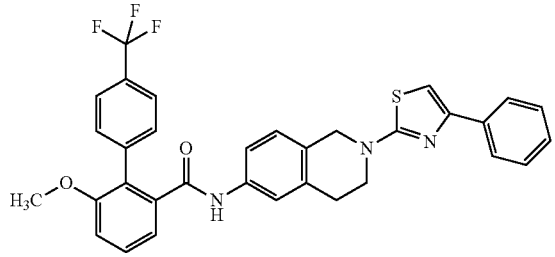

14

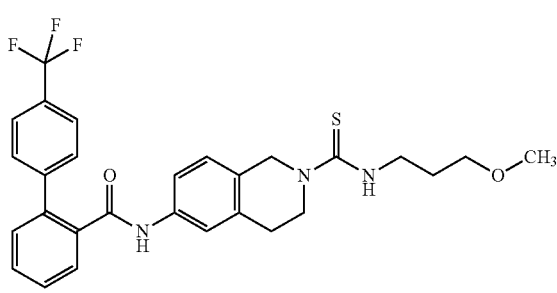

15

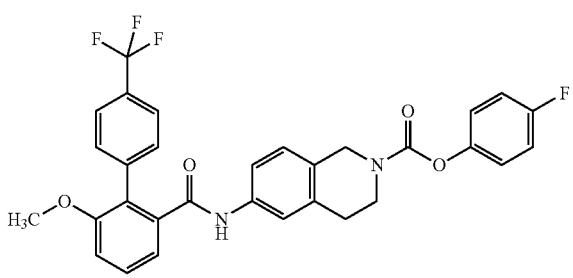

16

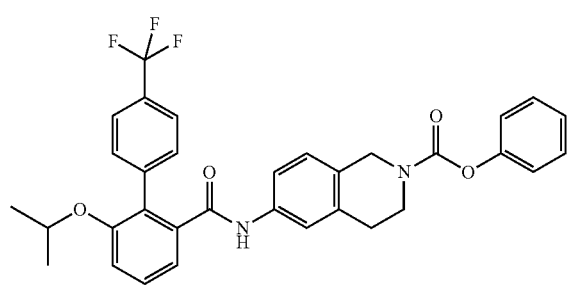

17

Compound Characterization

Compound 15

HPLC shows a retention time of 9.351 minutes with a $C_{16}$ column and 5-95% acetonitrile gradient over 10 minutes. High resolution mass spectrometry shows an $(M+Na)^+$ peak consistent with the molecular weight. $^1H$ and $^{13}C$ NMR spectroscopy are consistent with the chemical structure.

Compound 6

HPLC shows a retention time of 8.996 minutes with a $C_{16}$ column and 5-95% acetonitrile gradient over 10 minutes. High resolution mass spectrometry shows an $(M+H)^+$ peak consistent with the molecular weight. $^1H$ NMR spectroscopy is consistent with the chemical structure.

Other compounds were characterized by $^1H$ NMR and $^{13}C$ NMR, mass spectroscopy, and HPLC, and were consistent with analytical data.

The MTP inhibitors of the invention exhibit selective inhibition activity towards HepG2-ApoB1 that is associated with the VLDL lipoproteins secreted by the intestine while remaining inert towards HepG2-ApoA1, which is related to HDL (Table 1). One desired characteristic of a compound is the combination of permeability as shown in the Caco-2 permeability assay and cellular activity as shown in the HepG2 and Caco-2 ApoB assays. These assays indicate that the compounds of the invention exhibit selective permeability. Such selective permeability may result in these compounds having the ability to permeate the intestinal membrane, but not cross it, which is expected to minimize side effects. The MTP inhibitor compounds of the invention are expected to exhibit selective activity in the intestine without exhibiting undesirable systemic exposure, when administered orally.

One skilled in the art would understand that, despite the full description provided herein, the present invention can be performed within a wide and equivalent range of conditions, formulations, and other parameters without affecting the scope of the invention or any embodiment thereof. Additional embodiments are within the scope of the appended claims.

The contents of any patents, patent applications, or other references cited in this specification are hereby incorporated by reference in their entireties.

What is claimed is:

1. A method of treating a condition selected from the group consisting of atherosclerosis, pancreatitis, obesity, hypercholesteremia, hypertriglyceridemia, hyperlipidemia, and diabetes, comprising administering to a mammal in need of such treatment an effective amount of a chemical compound having Formula 1, such that the condition is treated Formula (I):

TABLE 1

| Cell Type/ Aqueous Solubility | 10 | 15 | 6 | 11 | 12 | 13 | 14 | 16 | 17 |
|---|---|---|---|---|---|---|---|---|---|
| IC50 HepG2 - Apo-B | 3 nM | 6 nM | 1 nM | 1.6 nM | 220 nM | 30 nM | 230 nM | 2.3 nM | 0.7 nM |
| IC50 HepG2 - ApoA1 | >30 μM | >30 μM | >30 μM | >30 μM | >30 μM | >30 μM | >30 μM | >30 μM | >30 μM |
| IC50 Caco-2 - Apo-B | 40 nM | 60 nM | 15 nM | 7.7 nM | 0.11 μM | 15 nM | 4400 nM | 11 nM | 16 nM |
| IC50 Caco-2 - ApoA1 | >30 μM | >30 μM | >30 μM | >30 μM | >30 μM | >30 μM | >30 μM | >30 μM | >30 μM |
| Caco-2 (10-6 cm/sec) | 0 | 0 | 0 | 0 | 0 | 30 | 0 | 0 | 0 |

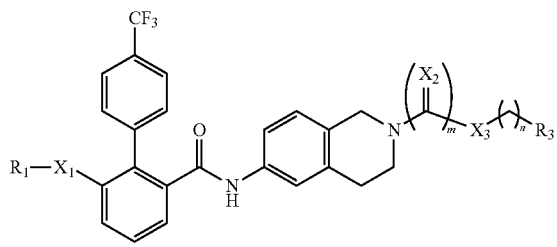

(I)

wherein:
R₁ is alkyl, R₄R₅NC(O)CH₂, cycloalkyl, heterocyclyl, or heterocyclylalkyl;
X₁ is a direct bond, O, S, —N(R₆)—, C(O)NR₆, or N(R⁶)C(O);
X₂ is O, —N(R₆)—, or S;
X₃ is a direct bond, O, —N(R₆)—, —CH₂—, arylene, or S;
R³ is H, alkyl, cycloalkyl, heterocyclyl, aryl, heteroaryl, heteroalkyl, aralkyl, alkylcarbonyl, alkoxycarbonyl, arylcarbonyl, aryloxycarbonyl, —OH, alkoxy, aryloxy, —SH, thioalkyl, thioaryl, or NR₄R₅;
R₄ and R₅ are, independently for each occurrence, H, alkyl, cycloalkyl, heterocyclyl, aryl, heteroaryl, heteroalkyl, aralkyl, alkylcarbonyl, alkoxycarbonyl, arylcarbonyl, or aryloxycarbonyl;
R₆ is, independently for each occurrence, H or alkyl;
m is 0 or 1; and
n is an integer from 0 to 3;
provided that if m is 0, X₃ is a direct bond or CH₂;
or a pharmaceutically acceptable salt, solvate, ester or hydrate thereof.

2. The method of claim 1, wherein said condition is selected from atherosclerosis, pancreatitis, obesity, and diabetes.

3. The method as defined in claim 1, wherein said condition is atherosclerosis.

4. A method of treating a condition selected from the group consisting of atherosclerosis, pancreatitis, obesity, hypercholesteremia, hypertriglyceridemia, hyperlipidemia, and diabetes, comprising administering to a mammal in need of such treatment an effective amount of a chemical compound having formula (II), such that the condition is treated formula (II):

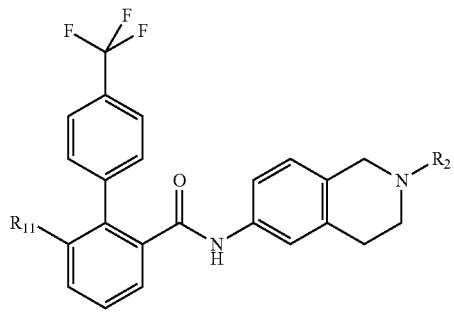

(II)

wherein R₁₁ is selected from:
H; H₃C—O—,

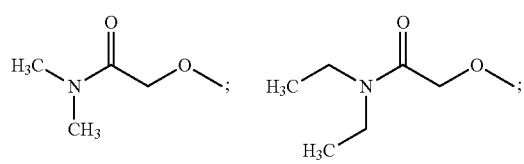

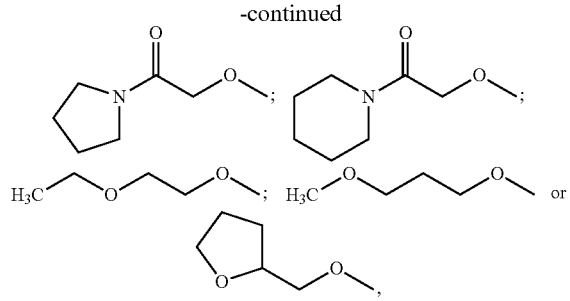

and R₁₂ is selected from:

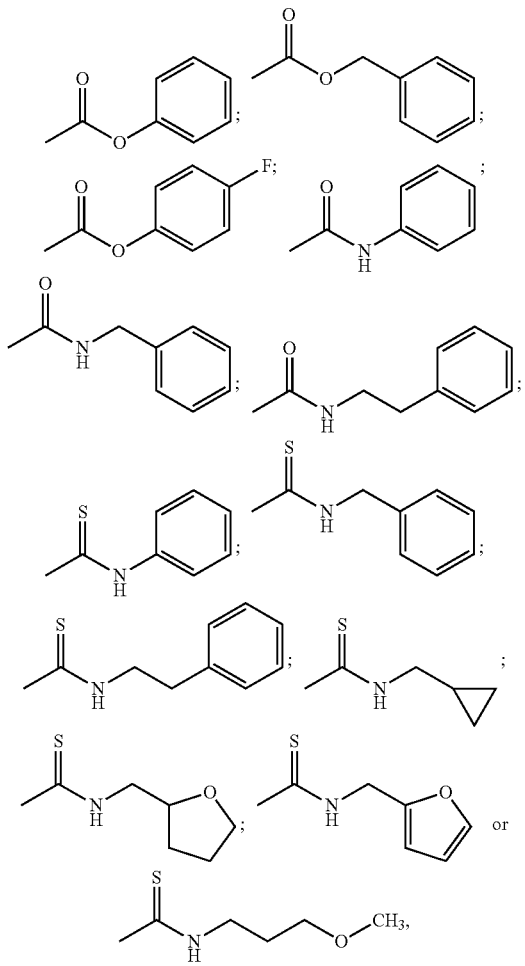

and pharmaceutically acceptable salts, esters, isomers, or solvate thereof.

5. The method of claim 4, wherein said condition is selected from atherosclerosis, pancreatitis, obesity, and diabetes.

6. The method as defined in claim 4, wherein said condition is atherosclerosis.

7. The method of claim 1, wherein the condition is diabetes.

8. The method of claim 4, wherein the condition is diabetes.

* * * * *